United States Patent
Hexsel

(12) 
(10) Patent No.: US 10,617,688 B2
(45) Date of Patent: Apr. 14, 2020

(54) USE OF PHARMACEUTICAL COMPOSITION FOR THE TREATMENT OF SKIN ERYTHEMA IN POIKILODERMAS

(71) Applicant: Doris Maria Hexsel, Porto Alegre (BR)

(72) Inventor: Doris Maria Hexsel, Porto Alegre (BR)

(*) Notice: Subject to any disclaimer, the term of this patent is extended or adjusted under 35 U.S.C. 154(b) by 0 days.

(21) Appl. No.: 16/087,580

(22) PCT Filed: Mar. 22, 2017

(86) PCT No.: PCT/BR2017/050070
§ 371 (c)(1),
(2) Date: Sep. 21, 2018

(87) PCT Pub. No.: WO2017/161432
PCT Pub. Date: Sep. 28, 2017

(65) Prior Publication Data
US 2019/0111055 A1 Apr. 18, 2019

(30) Foreign Application Priority Data
Mar. 22, 2016 (BR) .......................... 10 2016 006249 7
Feb. 27, 2017 (BR) .......................... 13 2017 004005 3

(51) Int. Cl.
| | |
|---|---|
| A61K 31/498 | (2006.01) |
| A61K 31/4174 | (2006.01) |
| A61K 31/4168 | (2006.01) |
| A61K 31/433 | (2006.01) |
| A61K 31/4458 | (2006.01) |
| A61K 31/137 | (2006.01) |
| A61K 31/155 | (2006.01) |
| A61K 31/198 | (2006.01) |
| A61P 17/00 | (2006.01) |
| A61K 31/421 | (2006.01) |
| A61K 31/165 | (2006.01) |
| A61K 31/4164 | (2006.01) |
| A61K 31/506 | (2006.01) |
| A61K 31/13 | (2006.01) |
| A61K 9/00 | (2006.01) |

(52) U.S. Cl.
CPC .......... *A61K 31/498* (2013.01); *A61K 31/13* (2013.01); *A61K 31/137* (2013.01); *A61K 31/155* (2013.01); *A61K 31/165* (2013.01); *A61K 31/198* (2013.01); *A61K 31/4164* (2013.01); *A61K 31/4168* (2013.01); *A61K 31/4174* (2013.01); *A61K 31/421* (2013.01); *A61K 31/433* (2013.01); *A61K 31/4458* (2013.01); *A61K 31/506* (2013.01); *A61P 17/00* (2018.01); *A61K 9/0014* (2013.01)

(58) Field of Classification Search
None
See application file for complete search history.

(56) References Cited

U.S. PATENT DOCUMENTS

| | | | |
|---|---|---|---|
| 2004/0242588 A1 | 12/2004 | Dejovin et al. | |
| 2011/0224216 A1 | 9/2011 | Andres et al. | |
| 2012/0082625 A1* | 4/2012 | Graeber ............... | A61K 9/0014 424/43 |

OTHER PUBLICATIONS

Fowler et al. in British Journal of Dermatology, 166(3): 633-641 (2012) (Year: 2012).*
Piwnica et al. In Drugs R.D. (2018) 18:87-90 (Year: 2018).*
International Search Report, PCT/BR2017/050070, dated Apr. 6, 2017, 6 pages, Rio de Janeiro, Brazil.
Alexander C. Katoulis, et al., Poikiloderma of Civatte and Rosacea: Variants in the Same Nosological Spectrum?, 2005, 2 pages, Athens, Greece.
Alexander C. Katoulis, et al., Poikiloderma of Civatte: a clinical and epidemiological study, 2005, 5 pages, Athens, Greece.
Alexander K.C. Leung, MD, et al., Poikiloderma of Civatte, 2016, 2 pages, Canada.
Supplemental European Search Report, EP 17 76 9197, dated Nov. 21, 2018, 6 pages, Munich, Germany.

* cited by examiner

*Primary Examiner* — Dennis Heyer
(74) *Attorney, Agent, or Firm* — Lambert Shortell & Connaughton; Gary E. Lambert; David J. Connaughton, Jr.

(57) ABSTRACT

The present invention pertains to the technological sector of the pharmaceutical industry and, more specifically, refers to a second use composition intended for the treatment of a dermatology condition called Poikiloderma of Civatte. The solution proposed in this document is the use of a topical composition containing any substance alone or in combination from the pharmacological group of alpha-adrenergic receptor agonists in therapeutic quantities to treat color of the lesions of Poikiloderma of Civatte. The application of this composition for the condition of Poikiloderma of Civatte results in significant improvement of the color of the skin lesions, also improving the vascular component present in this condition and can be associated with other compounds.

14 Claims, 2 Drawing Sheets

[Fig. 1]
[Fig.2]

[Fig.3]
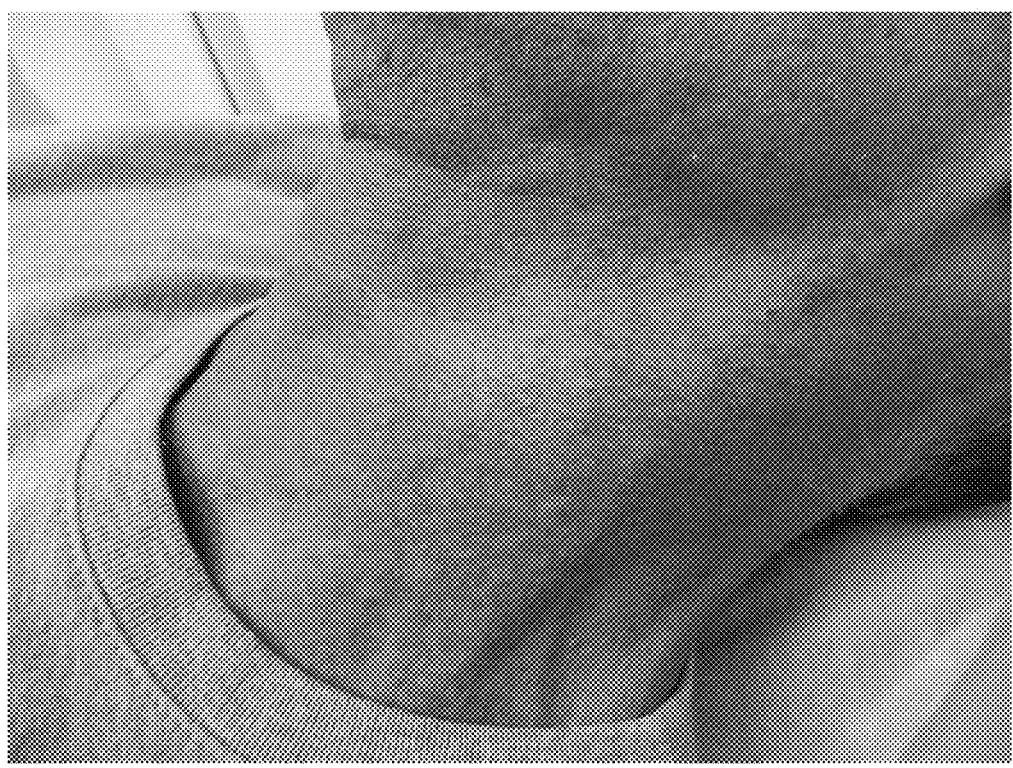

USE OF PHARMACEUTICAL COMPOSITION FOR THE TREATMENT OF SKIN ERYTHEMA IN POIKILODERMAS

CROSS-REFERENCE TO RELATED APPLICATIONS

The present application claims priority to PCT Patent Application No. PCT/BR2017/050070 filed on Mar. 22, 2017 which claims to priority to Brazilian Patent Application No. BR 10 2016 006249 7 filed on Mar. 22, 2016 and Brazilian Patent Application No. BR 13 2017 004005 3 filed on Feb. 24, 2017, the disclosures of which is incorporated herein by reference.

STATEMENT RE: FEDERALLY SPONSORED RESEARCH/DEVELOPMENT

Not Applicable

BACKGROUND

1. Technical Field

In a general manner, the present invention belongs to the technological sector of the pharmaceutical industry, and more specifically refers to a second use composition designed for the treatment of Poikiloderma of Civatte lesions.

2. Related Art

In 1923, the French dermatologist Civatte described three cases of middle-aged women who had net-like skin lesions symmetrically distributed and that manifested itself only in certain regions, especially on the face and neck. These lesions evolved slowly and insidiously, characterized by erythema, pigmentation and atrophy. Civatte then described the histopathological findings of two clinically different areas: in the area of the erythematous and in the atrophic area.

The term Poikiloderma refers to the combination of atrophy, telangiectasia, and pigmentary changes (hypo and hyper pigmentation). Patients presenting Poikiloderma of Civatte usually complain of a chronic reddish-brown coloration on the side of the cheeks and neck, sometimes affecting the chest as well. In this sense, there are clearly two components of major clinical importance in this condition: vascular changes that appear to varying degrees and pigmentary changes. The vascular component of Poikiloderma of Civatte (PC) may be present in varying degrees in different patients, manifesting itself by erythema as a consequence the appearance of small superficial elangiectasias on the skin of the lesions.

The disease predominantly affects the throat, neck and face of men and women and, in most patients, this condition is primarily aesthetic. The erythematous plaques associated with pigmentation and protruding hair follicles are usually asymptomatic and affect both sides of the neck. The condition usually affects light-skinned middle-aged or elderly patients, being more common in women than in men.

A large number of patients suffer from this condition, but the true number is unknown. The etiology is still not completely understood. The occurrence of PC in patients may be associated with some factors already singled out and observed in the literature: a) Chronic exposure to ultraviolet light seems to be a primary etiological factor, which is supported by the presence of solar elastosis in histopathological samples and the fact that the lesions relating to this condition occur on body areas exposed to the sun, saving the anatomically-covered regions; b) The presence of this condition in people from the same family and of both sexes, in successive generations, strongly suggests the involvement of genetic predisposition in the etiology of this condition. Genetically determined predisposition can be expressed by an increase in the susceptibility of the skin to ultraviolet radiation; c) Photosynthesizing agents present in perfumes or cosmetics have also been mentioned in literature as being a factor involved, which could act as triggers or aggravators in individuals hypersensitive to contact; d) Normal aging of the skin may be another factor, since it occurs in more elderly individuals; and e) Hormonal factors may be also involved, as its occurrence is relating to gender and age.

Genetically predisposed people can prevent the appearance of blemishing by avoiding exposure to direct sunlight, especially in the sunnier periods of the day. The use of sunscreen is also recommended for persons already diagnosed with this condition, as well as those with cases of Poikiloderma of Civatte in the family.

Currently, there is no medical treatment for this condition. For pigmentary changes, some available treatments may provide some cosmetic results to patients. On the other hand, for these patches,—there is still need for safer and more effective treatments. The methods of soothing the symptoms of Poikiloderma of Civatte currently provided are based on the use of lights and lasers systems that operate through the principle of selective photothermolysis, i.e. thermal damage confined to specific targets in the tissue. Clinical studies are using technologies of Pulse Dye Lasers and intense pulsed light to alleviate this skin condition, however the results thus far have been unsatisfactory, even after several sessions. In addition, several attempts of treatment were made, such as hydroquinone, electrosurgery, chemical peelings, argon laser and cryotherapy, but they were inefficient or presented undesirable adverse effects. Thus, it can be ascertained that the PC lacks successful treatments that can treat the combination of signs and symptoms of this condition.

Among the procedures for treating and/or alleviating the symptoms of patients with Poikiloderma of Civatte, we can mention a few methods and/or pharmaceutical formulations that are objects of patents and seek alternatives for the symptoms of the dermatological condition in question. North American patent of invention no number U.S. Pat. Nos. 9,220,788 9,220,788—"Nanoparticle and polymer formulations for thyroid hormone analogs, antagonists, and formulations and uses thereof", which despite disclosing methods of treating individuals with conditions related to angiogenesis, including the administration of a number of polymeric nanoparticles for thyroid hormone agonists, in an additional aspect, such treatment proves effective for other conditions sensitive to treatment by inhibition of angiogenesis as in the case of the Poikiloderma of Civatte, among others.

Another alternative consists of U.S. Pat. No. 9,102,687—"Ingenol-3-acylates III and ingenol-3-carbamates" in which there are described compounds of general formula (I) with the pharmaceutically acceptable salts, hydrates, or solvates thereof, for use in isolation or in combination with other compounds. Such compounds are recommended for therapy, prevention, treatment or improvement of diseases or conditions that respond to oxidative stimulation of neutrophils and in this context is used for cosmetic indications for, but not limited to, the treatment of various clinical conditions, including Poikiloderma of Civatte.

North American Patent Application No. U.S. 61/254,805-"Methods of treating or preventing acute erythema" describes treatment methods for skin conditions that appear "suddenly" or in an acute form, with compositions comprising an alpha-adrenergic receptor agonist, preferably brimonidine. However, this proposed method is only designed for treating acute erythema, preferably rosacea, and cases where erythema appears after medical procedures. The present solution does not provide for the treatment of acute onset conditions but rather when the PC has a slow onset of brownish erythema and chronic and progressive evolution, as in cases of Poikiloderma of Civatte. Again, it is important to mention that Poikiloderma of Civatte, also known as sun aging, is a condition caused by sun exposure and in any way will appear suddenly as disclosed in claim 2 of this prior art. Instead it is a persistent condition of the skin where the patient will notice darkened skin color (hyperpigmentation) and lightened skin color (hypopigmentation) as well as redness (erythema) characterized by the presence of fine blood vessels in the skin.

North American Patent Application No. U.S. Ser. No. 10/853,585—"Compounds, formulations, and methods for treating or preventing rosacea" describes treatment methods for skin conditions called rosacea, which is a common inflammatory skin disorder that result in unsightly and painful rashes, acne, persistent red veins, and acne-like skin eruptions, such as macules, nodules, and pustules that may ooze or crush. More advanced rosacea is characterized by a vascular stage where patients display increasingly severe erythema (abnormal redness of the skin) and telangiectasia (visible red lines due to abnormal dilatation of capillary vessels and arterioles). Pimple-like eruptions, which may be solid (called papules or nodules) or puss filled (known as pustules) may developed as well. The symptoms are often aggravated by sun exposure, changes or extremes in temperature, wind, and consumption of certain foods, such as spicy foods, caffeine, and alcohol. Despite the fact this patent application refers to the same drugs, different from Rosacea, the Poikiloderma of Civatte is not painful as no eruptions are presented or aggravated from external factors other than sun exposure or high temperatures, wind or food allergies. Instead, Poikiloderma of Civatte is slowly installed (mainly by exposing the skin to the sun) in specific regions of the body (cheeks, neck, chest) presenting the abovementioned symptoms of persistent redness, skin atrophy and telangiectasia.

However, although there are alternative treatments and/or alleviation of symptoms of the condition of Poikiloderma of Civatte, most of these solutions present the drawback of being composed of substances that damage the skin and cause many side effects. Thus, currently there is a gap in the field of medicines for the treatment of conditions of Poikiloderma of Civatte and, particularly, of the vascular component of this condition, capable of acting effectively and with least possible number of side effects.

BRIEF SUMMARY

The present invention relates to new compositions that use substances from the pharmacological group of alpha-adrenergic receptor agonists, in different concentrations or pharmaceutical compositions, and may or may not be associated with other compounds, to be used for treating Poikiloderma of Civatte. The application of topical products containing exclusively one alpha-adrenergic receptor agonist substance in isolation alone or in association with other compounds results in significant improvement of the color of the skin lesions of this dermatological condition.

One of the substances that can be used in said composition is topical brimonidine, which is an alpha-2-adrenergic agonist (belonging to the group of alpha-adrenergic agonists) and was initially used to lower intraocular pressure in patients with glaucoma or ocular hypertension. The development of drugs for vasoconstriction of the blood vessels is important to show improvement in the conditions that cause erythema on the skin of patients. Since brimonidine is an alpha-adrenergic agent, using compositions containing this active is an effective alternative to the brownish redness of Poikiloderma of Civatte.

BRIEF DESCRIPTION OF THE DRAWINGS

FIG. 1 represents the delimited area of the patient's skin to be treated with a composition described in this document, containing an alpha-adrenergic agonist, namely brimonidine gel 0.33%, prior to applying the medicine.

FIG. 2 represents the area of the patient's skin to be treated with the composition mentioned above, immediately after applying the medicine.

FIG. 3 represents the area of the patient's skin to be treated with the composition proposed in the present document, approximately 40 minutes after applying the medicine, showing its bleaching effects.

DETAILED DESCRIPTION

The present invention proposes the use of a pharmaceutical composition with efficacy in the treatment of erythema of the skin lesions of patients with Poikiloderma of Civatte. The composition in question consists of any active substance of the drug group of alpha-adrenergic receptor agonists and sufficient quantity of a pharmaceutically acceptable carrier.

This document discloses the effect of topical use of an active substance belonging to the group of alpha-adrenergic receptor agonists, in this case exemplified by brimonidine between 0.20% and 0.40%. Another drug belonging to the same pharmacological group can also be used in therapeutic concentrations in order to act in such a way as to cause vasoconstriction of the blood vessels. The composition in question is then applied on the skin lesions of the Poikiloderma of Civatte which have reddish appearance. Thus, the topical composition with the active ingredient can also be associated with other compounds to treat other skin alterations of Poikiloderma of Civatte, such as hyperpigmentation, or atrophy. In this case, the active substance could be associated with bleaching agents or compounds that fight the cutaneous atrophy, to treat the main components of Poikiloderma: hyperpigmentation, redness, and atrophy.

Drawings 1, 2 and 3 accompanying this patent application demonstrate the effectiveness of the application of using compositions containing the active ingredient brimonidine in patients presenting redness and pigmentation on Poikiloderma of Civatte lesions. Drawing 1 represents the area selected and marked with white pencil for applying a product containing the alpha-adrenergic agonist brimonidine at 0.33% on skin lesions of Poikiloderma of Civatte; this drawing represents the area prior to application. Drawing 2 represents the moment immediately after applying the composition, which was restricted to the small area marked on the skin of the patient. Lastly, drawing 3 shows the area where the proposed composition was applied, with effective improvement in the color of the skin affected by Poikiloderma of Civatte, 40 minutes after applying the medicine. It is pointed out that the effects of this medicine tend to increase gradually in the first 1 to 3 hours, and decrease after 6 to 9 hours, so it is recommended that the product be applied in the morning or up to 6 hours before the patient looks for the effects. It is noted that applying this product to the Poikiloderma of Civatte erythema visibly improves the redness of the condition. It was demonstrated that the adverse events reported in clinical studies for the treatment of acute erythema or diseases such as rosacea were less than or equal to 1%, the most common being erythema, redness, burning sensation and contact dermatitis.

Thus, not only is brimonidine disclosed, but also other examples of substances belonging to the group of alpha-adrenergic receptor agonists which may be used analogously, but not limited to: apraclonidine, clonidine, desglymidodrine, dexmedetomidine, dopamine, ephedrine, epinephrine, epinine (N-methyl dopamine), ethylnorepinephrine, phenylephrine, phenylpropanolamine, guanabenz, guanfacine, 1-dobutamine, levarterenol, lofexidine, mephentermine, metaraminol, methylphenidate, methoxamine, midodrine, mytodrine, mivazerol, moxonidine, naphazoline, norepinephrine, norphenylephrine, oxymetazoline, pemoline propylhexedrine, propylhexedrine, tetryzoline, tizanidine, xylometazoline, α-methyldope, α-methylnorepinephrine, (4.5-dihydro-1H-imidazol-2-yl)-(quinoxaline-8-methyl-6-yl)-amine, (4.5-dihydro-1h-imidazol-2-yl) quinoxaline-5-yl-amine, (5-bromo-2-methoxy-quinoxaline-6-yl)-(4.5-dihydro-1h-imidazol-2-yl)-amine, (5-bromo-3-methyl-6-yl) quinoxaline-(4.5-dihydro-1h-imidazol-2-yl)-amine, (8-bromo-quinoxalin-5-yl)-(4.5-dihydro-1h-imidazol-2-yl)-amine, (8-bromoquinoxalin-6-yl)-(4.5-dihydro-1h-imidazol-2-yl)-amine.

The Poikiloderma consists in the appearance of pigmentation and small vessels called telangiectasias, evolving chronically and progressively. In this sense, it is important to highlight that in this skin condition, the color of the lesions tends to increase gradually with time/advancement of age, with no reversal of this condition, which is usually not the case of the current indications of the available alpha-adrenergic receptor agonists, including brimonidine and oxymetazoline (which are currently used for cases of acute erythema, such as rosacea).

Additionally, a range of topical compositions can be produced with the active compounds mentioned above, such as creams, solutions, gels, cream lotions, ointments, foams, mousses, emulsions, microemulsions, soaps, bars, corrective cosmetics and sunscreen, powders and foundations. Said active substances belonging to the pharmacological group of alpha-adrenergic receptor agonists may also be applied using methods that increase the penetration thereof, such as micro-needles, lasers, ionization and ultrasound.

It is important to emphasize that the description does not have the effect of limiting the ways of implementing the inventive concept now proposed. Therefore, the descriptions should be interpreted in an illustrative and non-limiting manner, as there may be other equivalent or similar forms of implementing the inventive concept now disclosed that do not stray from the scope of protection outlined in the proposed solution.

This specification addressed dermatological compositions for topical use containing an active substance belonging to the group of pharmacological alpha-adrenergic receptor agonists for the treatment of erythema of Poikiloderma of Civatte, endowed with novelty, inventive step, demonstrative and full disclosure, industrial application and, consequently, satisfies all the essential requirements for the granting of the privilege claimed.

The invention claimed is:
1. A method of Use of a pharmaceutical composition for the treatment of poikilodermas comprising the steps of: applying an active substance from the pharmacological group of alpha-adrenergic receptor agonists to a skin lesion of Poikiloderma of Civatte.

2. The method of use of a pharmaceutical composition for the treatment of poikilodermas according to claim 1, wherein the active substance is at least one of a compound selected from the group consisting of: apraclonidine, brimonidine, clonidine, desglymidodrine, dexmedetomidine, dopamine, ephedrine, epinephrine, epinine (N-methyl dopamine), ethylnorepinephrine, phenylephrine, phenylpropanolamine, guanabenz, guanfacine, 1-dobutamine, levarterenol, lofexidine, mephentermine, metaraminol, methylphenidate, methoxamine, midodrine, mytodrine, mivazerol, moxonidine, naphazoline, norepinephrine, norphenylephrine, oxymetazoline, pemoline propylhexedrine, propylhexedrine, tetryzoline, tizanidine, xylometazoline, α-methyldope, α-methylnorepinephrine, (4.5-dihydro-1H-imidazol-2-yl)-(quinoxaline-8-methyl-6-yl)-amine, (4.5-dihydro-1h-imidazol-2-yl) quinoxaline-5-yl-amine, (5-bromo-2-methoxy-quinoxaline-6-yl)-(4.5-dihydro-1h-imidazol-2-yl)-amine, (5-bromo-3-methyl-6-yl) quinoxaline-(4.5-dihydro-1h-imidazol-2-yl)-amine, (8-bromo-quinoxalin-5-yl)-(4.5-dihydro-1h-imidazol-2-yl)-amine, and (8-bromoquinoxalin-6-yl)-(4.5-dihydro-1h-imidazol-2-yl)-amine.

3. The method of use of a pharmaceutical composition for the treatment of poikilodermas according to claim 1, wherein the active substance from the group of alpha-adrenergic receptor agonists is associated with lightener compounds.

4. The method of use of a pharmaceutical composition for the treatment of poikilodermas according to claim 2, wherein the active substance is brimonidine is present in therapeutic concentrations varying between 0.25% and 0.40%.

5. The method of use of a pharmaceutical composition for the treatment of poikilodermas according to claim 4, wherein the active substance brimonidine is present in a therapeutic concentration of 0.33%.

6. The method of use of a pharmaceutical composition for the treatment of poikilodermas according to claim 4, wherein the active substance brimonidine is present preferably in a therapeutic concentration of 0.35%.

7. The method of use of a pharmaceutical composition for the treatment of poikilodermas according to claim 2, wherein the active substance comprises at least two compounds, each of the at least two compounds belonging to the same pharmacological group and at least one of the at least two compounds promote vasoconstriction, specifically improving the color of the skin and erythema caused by the telangiectasias and pigmentation present in the lesion of Poikiloderma of Civatte.

8. The method of use of a pharmaceutical composition for the treatment of poikilodermas according to claim 2, wherein the active substance comprises at least two compounds, wherein each of the at least two compounds may be used in isolation or combined with each other.

9. The method of use of a pharmaceutical composition for the treatment of poikilodermas according of claim 4 wherein the applying step results in a reducing of a redness of the lesion of Poikiloderma of Civatte.

10. The method of use of a pharmaceutical composition for the treatment of poikilodermas according of claim 9 wherein the active substance is selected such that the applying step causes the reducing of a redness of the lesion which increases gradually over a time period of one to three hours after the applying step, and decreases gradually six to nine hours after the applying step.

11. The method of use of a pharmaceutical composition for the treatment of poikilodermas according of claim 4 wherein the active substance further comprises a second alpha-adrenergic receptor agonist different from the brimonidine, the second alpha-adrenergic receptor agonist selected to cause a vasoconstriction of blood vessels of the skin to which the active substance is applied.

12. The method of use of a pharmaceutical composition for the treatment of poikilodermas according of claim 4 wherein the active substance further comprises a second alpha-adrenergic receptor agonist different from the brimonidine, the second alpha-adrenergic receptor agonist selected to be a bleaching agent.

13. The method of use of a pharmaceutical composition for the treatment of poikilodermas according of claim 4 wherein the active substance further comprises a second alpha-adrenergic receptor agonist different from the brimonidine, the second alpha-adrenergic receptor agonist selected to be a bleaching agent.

14. The method of use of a pharmaceutical composition for the treatment of poikilodermas according of claim 4 wherein the active substance further comprises a second alpha-adrenergic receptor agonist different from the brimonidine, the second alpha-adrenergic receptor agonist selected to fight cutaneous atrophy.

\* \* \* \* \*